US00PP21540P2

(12) United States Plant Patent
Knight et al.

(10) Patent No.: US PP21,540 P2
(45) Date of Patent: Nov. 30, 2010

(54) CRAPEMYRTLE PLANT NAMED 'CHOCOLATE MOCHA'

(50) Latin Name: *Lagerstroemia indica×Lagerstroemia indica×fauriei*
Varietal Denomination: Crapemyrtle 'Chocolate Mocha'

(75) Inventors: Patricia R. Knight, Biloxi, MS (US); Wayne J. McLaurin, Poplarville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 12/455,315

(22) Filed: May 29, 2009

(51) Int. Cl.
*A01H 5/00* (2006.01)

(52) U.S. Cl. ..... Plt./252

(58) Field of Classification Search ..... Plt./252
See application file for complete search history.

*Primary Examiner*—Annette H Para
(74) *Attorney, Agent, or Firm*—Lawrence Arthur Schemmel

(57) ABSTRACT

A new and distinct variety of *Lagerstroemia* crapemyrtle plant named 'Chocolate Mocha', characterized by its combination of deep dark brown/red-purple leaf color and brilliant bubble gum pink flower color. 'Chocolate Mocha' is also distinguished by its resistance to leaf scorch, upright non-spreading growth, and medium growth size.

3 Drawing Sheets

STATEMENT OF GOVERNMENT SUPPORT

This invention was made with government support under 58-6404-0-014 awarded by the U.S. Department of Agriculture. The government may have certain rights in the invention.

Botanical classification: *Lagerstroemia indica×Lagerstroemia indica×fauriei.*

Varietal denomination: Crapemyrtle 'Chocolate Mocha'.

BACKGROUND OF THE INVENTION

The present invention relates to a new and very distinct variety or cultivar of the ornamental flowering shrub and landscape plant of the genus *Lagerstroemia*, commonly known as crapemyrtle, of the family Lythraceae, and is referred to hereinafter by its varietal denomination 'Chocolate Mocha'. This novel plant is an asexually propagated hybrid of crapemyrtle that was selected in 2003 from approximately 3600 identified crosses. The female seed parent is *Lagerstroemia indica* 'Whit IV' ("Red Rocket"), U.S. Pat. No. 11,342. The male pollen parent is *Lagerstroemia indica×fauriei* 'Sarah's Favorite' (unpatented). 'Chocolate Mocha' was selected for its unusual and brilliant bubble gum pink flower color and other distinctive features. The designation 'Chocolate Mocha' was evaluated under the experimental name 'CREC 2003-01'. This high quality novel and distinct variety of crapemyrtle plant was vegetatively propagated at the Mississippi State University Coastal Research and Extension Center, South Mississippi Branch Experiment Station, in Poplarville, Miss. Each of several generations of cuttings has produced stable plants identical to the original seedling plant.

SUMMARY OF THE INVENTION

The cultivar 'Chocolate Mocha' is a distinctive, new variety of crapemyrtle plant characterized by its brilliant bubble gum pink flower color and unique dark brown/red-purple leaf color. The traits of the invention are continually maintained when propagated asexually. This new variety may vary slightly with changes in location, temperature, light, and other environmental conditions, but the genotype will not be affected. 'Chocolate Mocha' also exhibits the quality and characteristic of adaptability to all areas of hardiness zones 7-10. Compared to its parents, its female parent 'Red Rocket' generally has light green leaves that fade through the growing season and red flower color. Red Rocket's new growth red leaf color is lighter than that of 'Chocolate Mocha'. The new plant's male parent 'Sarah's Favorite' generally has medium green leaves and white flower color. The combination of Chocolate Mocha's dark brown/red-purple leaf color and brilliant pink flower color distinguishes it from these and all other crapemyrtle cultivars.

BRIEF DESCRIPTION OF THE DRAWINGS

The color photographs illustrate the unique characteristics of leaf and flower color of the new variety. The photographs show the colors as true as is reasonably possible to obtain with current photographic techniques. Colors in the photographs may differ from the actual colors and values in the description of the new crapemyrtle plant due to light conditions and other factors.

DETAILED BOTANICAL DESCRIPTION OF THE VARIETY

The following is a detailed botanical description of the characteristics of the new *Lagerstroemia* crapemyrtle variety known as 'Chocolate Mocha', based on observations of the plant grown at the Coastal Research and Extension Center and research facility at Poplarville, Miss., and under similar conditions to those for growing these plants commercially. 'Chocolate Mocha' has been observed under many but not all possible environmental conditions. Color notations of plant tissues are based upon The Royal Horticulture Society (R.H.S.) Colour Chart, 2001 Edition. Color notations may have been slightly affected by light quality and fertility and general plant growth. Certain characteristics will vary depending on the age of the plants so that dimensions, sizes, and colors are approximations or averages since the variety has not been observed under every possible environmental condition. Therefore, the phenotype of the variety may differ from the descriptions depending upon environmental variations including but not limited to the season, temperatures, day lengths, light direction and quality, and fertilization, as well as other factors.

This new plant is a *Lagerstroemia* hybrid resulting from the cross of *Lagerstroemia indica* 'Whit IV' (female parent) and *Lagerstroemia indica×fauriei* 'Sarah's Favorite' (male parent). The stem color of this novel plant is dark red (R.H.S. Colour Chart Greyed-Purple Group #183A). The leaf color is a dark-brownish-red/purple (R.H.S. Colour Chart Brown Group #200A). The flower petal color is pink (R.H.S. Colour Chart Red-Purple Group color #68A).

Figure 1:
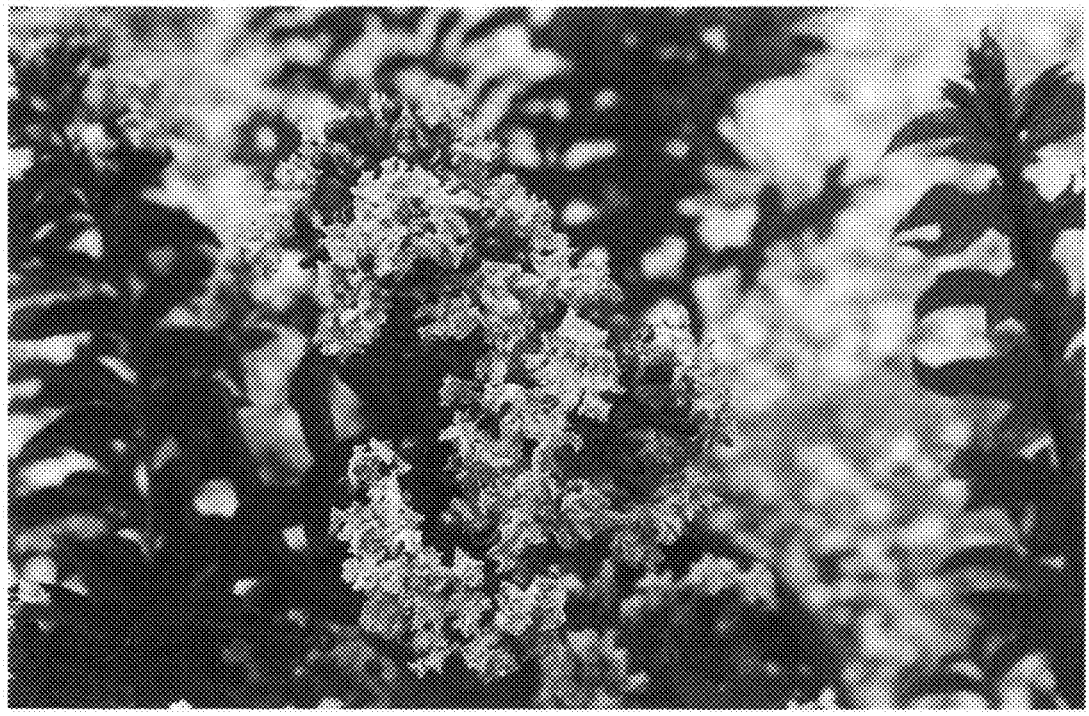
FIG. 1 is a color photograph of the new crapemyrtle 'Chocolate Mocha' taken at the Coastal Research and Extension Center, South Mississippi Branch Experiment Station, that shows the flower color against a background of the leaf color of the new cultivar.

FIG. 1 shows the flower color and the leaf color of the new cultivar.

Figure 2:
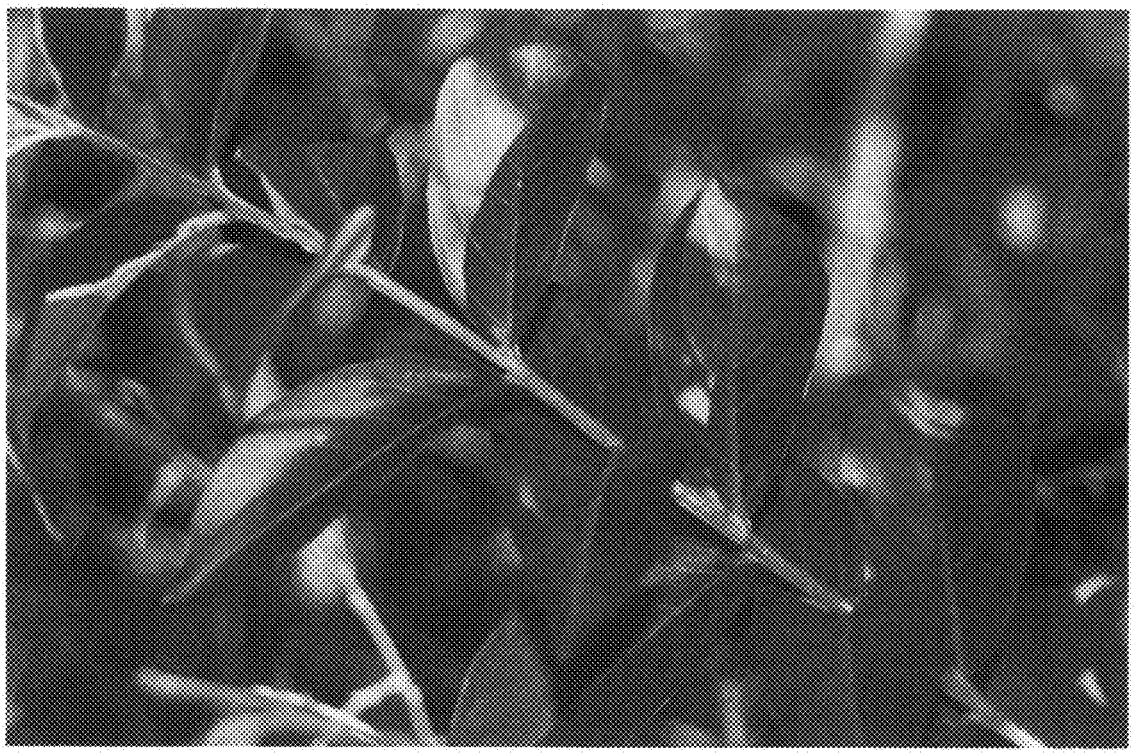
FIG. 2 is a color photograph of the new crapemyrtle 'Chocolate Mocha' taken at the Coastal Research and Extension Center South Mississippi Branch Experiment Station, that shows the leaf color and the twig color of the new cultivar.

FIG. 2 shows the leaf color and twig color of the new cultivar.

Figure 3:
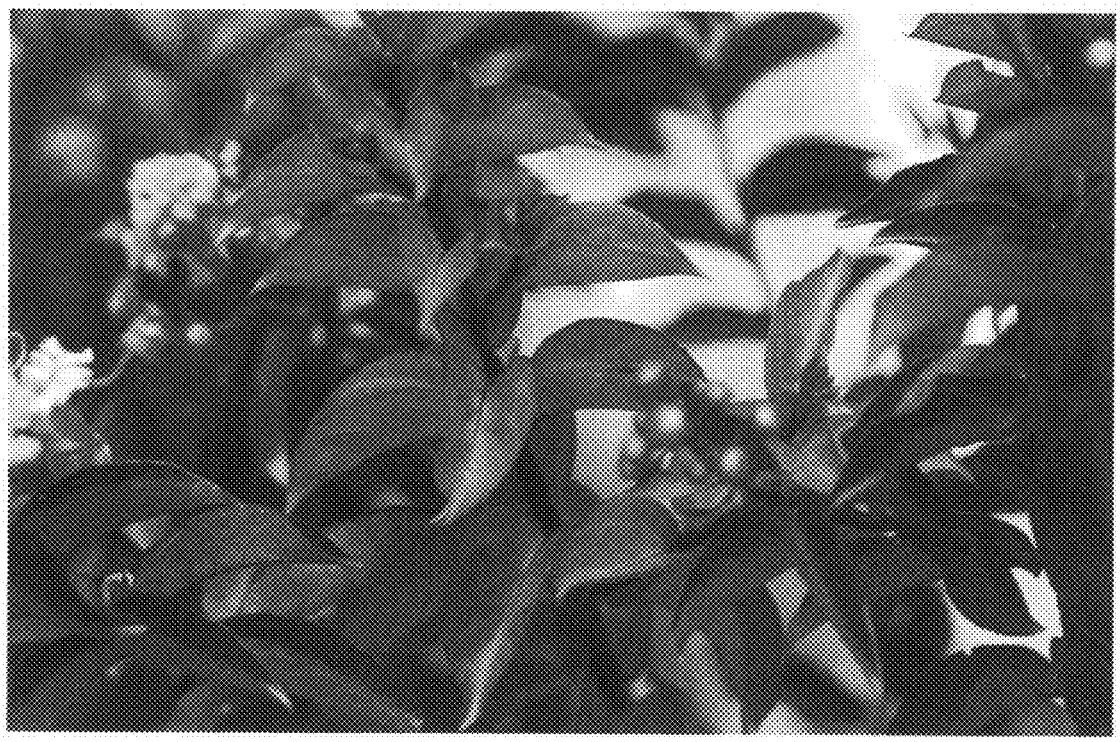
FIG. 3 is a color photograph of the new crapemyrtle 'Chocolate Mocha' taken at the Coastal Research and Extension Center South Mississippi Branch Experiment Station, that shows new growth of the new cultivar with older growth in the background.

FIG. 3 shows new cultivar growth in the foreground and old growth in the background.

The plant has unique foliage color that can easily be used as a centerpiece or accent specimen in landscapes where other crapemyrtle plants are traditionally used as well. The leaves of this new plant do not exhibit leaf scorch problems that are typically associated with dark-leaved plants in the deep southern parts of the U.S. 'Chocolate Mocha' also has unique foliage color that remains and is maintained throughout the growing season. The dark brownish red/purple foliage and the flowers, which are a complementary brilliant medium bubble gum pink color, provide a combination that no other crapemyrtle plant possesses.

The final height and width of the plant have not been observed. Three-year plants in the research facility at the South Mississippi Branch Experiment Station are approximately 6 to 7 feet tall and approximately 3 to 3.5 feet wide, exhibiting an upright non-spreading growth forming a multiple or single trunk large shrub to small tree. Its foliage comprises glossy, dark purple/red leaves that are opposite and that are approximately from 1.75 to 2.5 inches in length and from 1.00 to 1.25 inches in width. New leaves generally begin as green and turn to purple/red. The leaf top color is RHS color 200A and the parts of the upper leaf that appear green are RHS color 137A. The leaf underside color is RHS color N77C. The leaf type is simple and is persistence and deciduous. The leaf margin is entire, the leaf shape is elliptical, and the leaf venation is pinnate. The leaf petiole is very short and is approximately less than ⅛ of an inch. New stem growth is purple turning to brown as the plant matures. The stem is rather slender, angled often almost squarish with rather prominent wings. The stem starts out reddish purple in color maturing to a gray to grayish brown color. As the variety is a deciduous, summer-flowering plant, the leaves do not show any fall color. The plant has shown some mildew tolerance under field conditions.

The flowers are perfect, 6-petaled and each flower is approximately 1.25 inches in diameter. The flowers are medium pink and are visible from June to August. The flowers have medium-long tapered panicles with an excess of 150 flowers per inflorescence. The flower panticle is approximately 4.5 inches in width and 6 inches in length. The unopened flower capsule color is RHS color 59A.

The fruit is comprised of seed pods that are purple in color turning to brown. The mature seed pod color is RHS color 184A. The fruit is a broad-ellipsoidal 6-valved dehiscent capsule, brown in color, approximately ½ of an inch wide and the seeds are approximately ⅜ of an inch long and winged. The pistil color is RHS color 7A. A woody capsule generally persists on the panicle until late winter. Cold testing for cold hardiness has not yet been completed for the new variety. The plant bark is typical of *Lagerstroemia* but had not exfoliated at the time of observation.

Rooting of the new medium-sized plant is easily accomplished, making the plant excellent for production purposes, and such rooted plants are identical to the original. The novelty of the plant includes its dark brown-red/purple leaf color and its ability to resist leaf scorch and color fading throughout the summer growing season. Its unique leaf color in combination with its unusual brilliant bubble gum pink flower color makes the new plant even more distinctive among traditional crapemyrtle plants. No other crapemyrtle plant has this combination of characteristics.

As will be apparent to those skilled in horticultural science, the new and distinct crapemyrtle plant variety described herein may vary in minor detail due to climatic, soil, and cultural conditions under which the variety may be grown, as well as the stage of growth.

What is claimed is:

1. A new and distinct variety of crapemyrtle plant, substantially as herein illustrated and described.

* * * * *